United States Patent
Neely

(10) Patent No.: US 6,489,332 B1
(45) Date of Patent: *Dec. 3, 2002

(54) A$_1$ ADENOSINE RECEPTOR ANTAGONISTS

(75) Inventor: Constance F. Neely, Raleigh, NC (US)

(73) Assignee: Endacea, Inc., Research Triangle Park, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/269,055

(22) PCT Filed: Nov. 19, 1997

(86) PCT No.: PCT/US97/21045

§ 371 (c)(1),
(2), (4) Date: Mar. 18, 1999

(87) PCT Pub. No.: WO98/22465

PCT Pub. Date: May 28, 1998

Related U.S. Application Data

(63) Continuation-in-part of application No. 08/753,048, filed on Nov. 19, 1996, now Pat. No. 5,786,360.

(51) Int. Cl.$^7$ ............... A61K 31/52; C07D 473/06; A61P 9/04; A61P 11/06; A61P 37/08
(52) U.S. Cl. ............... 514/263.35; 544/271; 544/272; 544/311; 544/312
(58) Field of Search ............... 544/271, 272; 514/263, 263.35

(56) References Cited

U.S. PATENT DOCUMENTS

| | | | |
|---|---|---|---|
| 2,887,486 A | 5/1959 | Leake et al. | 260/253 |
| 3,031,451 A | 4/1962 | Schlesinger et al. | 260/253 |
| 3,309,271 A | 3/1967 | Georges et al. | 167/55 |
| 3,317,533 A | 5/1967 | De Ridder | 260/253 |
| 3,961,060 A | 6/1976 | Fuxe | 424/253 |
| 4,092,417 A | 5/1978 | Credner et al. | 424/253 |
| 4,299,832 A | 11/1981 | Brown et al. | 424/253 |
| 4,378,359 A | 3/1983 | Chiodoni et al. | 424/248.57 |
| 4,548,818 A | 10/1985 | Kjellin et al. | 514/263 |
| 4,612,315 A | 9/1986 | Jacobson et al. | 514/263 |
| 4,622,324 A | 11/1986 | Klessing et al. | 514/265 |
| 4,696,932 A | 9/1987 | Jacobson et al. | 514/263 |

FOREIGN PATENT DOCUMENTS

| | | | |
|---|---|---|---|
| BE | 636 828 A | | 3/1964 |
| DE | 1 245 383 | | 7/1967 |
| DE | 26 59 241 | | 7/1978 |
| EP | 0 501 379 A | | 9/1992 |
| EP | 0 503 563 A2 | | 9/1992 |
| EP | 0764 647 | | 3/1997 |
| FR | 2 483 922 | | 12/1981 |
| GB | 947495 | | 1/1964 |

OTHER PUBLICATIONS van Galen et al.; "Adenosine A$_1$ and A$_2$ Receptors: Structure–Function Relationships," *Medicinal Research Reviews* 12:423–471 (Sep. 1992).

(List continued on next page.)

Primary Examiner—Mark L. Berch
(74) Attorney, Agent, or Firm—Myers Bigel Sibley & Sajovec

(57) ABSTRACT

A compound useful as an A$_1$ adenosine receptor antagonist has the formula:

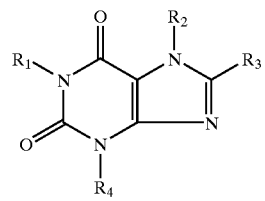

wherein

R$_1$ is selected from the group consisting of C$_1$–C$_8$ alkyl;

R$_2$ is of the formula:

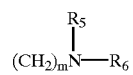

wherein is an integer ranging from 1 to 8; R$_5$ is H or (CH$_2$)$_p$, wherein p is an integer ranging from 1 to 8 and R$_6$ is H or (CH$_2$)$_m$OH, wherein m is an integer ranging from 1 to 8;

R$_3$ is of the formula:

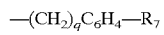

wherein q is an integer ranging from 1 to 8; and wherein R$_7$ is selected from the group consisting of H, NH$_2$, (CH$_2$)$_t$OH, wherein t is an integer ranging from 1 to 8; and R$_9$COOH, wherein R$_9$ is an alkyl or alkylidene group having 1 to 8 carbon atoms; and R$_4$ is of the formula:

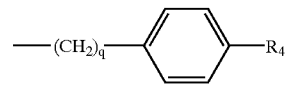

wherein R$_s$ is selected from the group consisting of H; NH$_2$; (CH$_2$)$_r$OH, wherein s is an integer ranging from 1 to 8; and R$_{10}$COOH wherein R$_{10}$ is an alkyl or alkylidene group having 1 to 8 carbon atoms; and r is an integer ranging from 1 to 8.

15 Claims, No Drawings

U.S. PATENT DOCUMENTS

| | | | |
|---|---|---|---|
| 4,769,377 A | 9/1988 | Snyder et al. | 514/263 |
| 4,772,607 A | 9/1988 | Badger et al. | 514/263 |
| 4,868,186 A | 9/1989 | Franzone et al. | 514/265 |
| 4,968,672 A | 11/1990 | Jacobson et al. | 46/514 |
| 4,971,972 A | 11/1990 | Doll et al. | 265/514 |
| 5,032,593 A | 7/1991 | Rzeszotarski et al. | 514/263 |
| 5,066,655 A | 11/1991 | Olsson | 514/261 |
| 5,068,236 A | 11/1991 | Suzuki et al. | 514/263 |
| 5,208,240 A | 5/1993 | Peet et al. | 514/263 |
| 5,248,770 A | 9/1993 | Jacobson et al. | 536/26.1 |
| 5,256,650 A | 10/1993 | Peet et al. | 514/46 |
| 5,296,463 A | 3/1994 | Lee et al. | 514/2 |
| 5,298,508 A | 3/1994 | Jacobson et al. | 514/263 |
| 5,314,890 A | 5/1994 | Agostini et al. | 514/263 |
| 5,340,813 A | 8/1994 | Klein et al. | 514/263 |
| 5,395,836 A | 3/1995 | Shimada et al. | 514/263 |
| 5,434,150 A | 7/1995 | Austel et al. | 514/228.5 |
| 5,447,933 A | 9/1995 | Suzuki et al. | 514/263 |
| 5,532,368 A | 7/1996 | Kufner-Muhl et al. | 544/267 |
| 5,543,415 A | 8/1996 | Suzuki et al. | 514/263 |
| 5,545,627 A | 8/1996 | Jacobson et al. | 514/46 |
| 5,719,279 A * | 2/1998 | Kufner-Muhl | 544/272 |
| 5,786,360 A * | 7/1998 | Neely | 544/272 |

OTHER PUBLICATIONS

Neely et al., *Caromed Intl, $A_1$ Adenosine Receptor Antagonists block Ischemia–Reperfusion Injury of the Heart*, vol. 94, No. 9 (Nov. 1, 1996).

Jacobson et al., *Molecular Pharmacology, A Functionalized Congener Approach to Adenosine Receptor Antagonists: Amino Acid Conjugates of 1,3–Dipropylxanthine*, vol. 29, pp. 126–133 (1985).

Van Galen et al., *J. Med. Chem., A Model for the Antagonist Binding Site on the Adenosine $A_1$ Receptor, Based on Steric, Electrostatic, and Hydrophobic Properties*, vol. 33, pp. 1709–1713 (1990).

Jacobson et al., *J. Med. Chem., Adenosine Receptors: Pharmacology, Structure–Activity Relationships, and Therapeutic Potential*, vol. 35, No. 3, pp. 407–422 (Feb. 7, 1992).

Windholz, *The Merck Index, Bamifylline*, Tenth Edition, p. 952 (1983).

*J. Med. Chem., Communications to the Editor*, vol. 35, pp. 3578–3581 (1992).

Abbracchio et al., *Pharmacological Research Communications, Selective Activity of Bamifylline on Adenosine $A_1$ — Receptiors in Rat Brain*, vol. 19, No. 8, pp. 537–545 (1987).

*BioWorld Today, Others News to Note*, pp. 2–4 (Mar. 20, 1996).

Belliardo et al., *Journal of Chromatography, Micro–Scale Liquid Chromatographic Method for the Determination of Bamifylline and its major Metabolite in human Plasma*, pp. 305–309 (1990).

Schiantarelli et al., *Arzneim.–Forsch., Evidence of Pulmonary Tropism of Bamifylline and its Main Active Metabolite*, pp. 215–219 (1989).

Van Rhee et al., *J. Med. Chem., Tetrahydrobenzothiophenone Derivitives as a Novel Class of Adenosine Receptor Antagonists*, vol. 39, pp. 398–406 (1996).

Muller et al., *J. Med. Chem., 7–Deaza–2–henyladenines: Structures–Activity Relationships of Potent $A_1$ Selective Adenosine Receptor Antagonists*, vol. 33, pp. 2822–2828 (1990).

Patel et al., *Molecular Pharmacology, I–BW–A844U, an Antagonist Radioligand with High Affinity and Selectivity for Adenosine $A_1$ Receptors, and $^{125}I$–Azido–BW–A844U, a Photoaffinity Label*, vol. 33, pp. 585–591 (1988).

Carlucci et al., *Journal of Pharmaceutical & Biomedical Analysis, Determination of Bamifylline Hydrochloride Impurities in Bulk Material and Pharmaceutical Forms Using Liquid Chromatography with Ultraviolet Detection*, vol. 8, pp. 1067–1069 (1990).

* cited by examiner

A₁ ADENOSINE RECEPTOR ANTAGONISTS

CROSS-REFERENCE TO RELATED APPLICATIONS

The instant application is a national phase application of PCT/US97/21045 filed Nov. 19, 1997 and is a continuation-in-part application of U.S. patent application Ser. No. 08/753,048 filed Nov. 19, 1996, now U.S. Pat. No. 5,786,360.

FIELD AND BACKGROUND OF THE INVENTION

The present invention relates to novel compounds useful as $A_1$ adenosine receptor antagonists.

Adenosine receptors are involved in a vast number of peripheral and central regulatory mechanisms such as, for example, vasodilation, cardiac depression, inhibition of lipolysis, inhibition of insulin release and potentiation glucagon release in the pancreas, and inhibition of neurotransmitter release from nerve endings.

In general, adenosine receptors can be divided into two main classes, $A_1$ receptors which can inhibit, and $A_2$ receptors which can stimulate adenylate cyclase activity. One of the best known classes of adenosine receptor antagonists are the xanthines which include caffeine and theophylline. See e.g., Müller et al., *J. Med. Chem.* 33: 2822–2828 (1990). In general, many of these antagonists often suffer from poor water solubility, and low potency or lack of selectivity for adenosine receptors. Additionally, selective analogues of adenosine receptor antagonists have been developed through the "functionalized congener" approach. Analogues of adenosine receptor ligands bearing functionalized chains have been synthesized and attached covalently to various organic moieties such as amines and peptides. Attachment of the polar groups to xanthine congeners has been found to increase water solubility. Nonetheless, such developments have yet to fully address problems associated with potency and selectivity. More recently Jacobson et al. *J. Med. Chem.* 35: 408–422 (1992) has proposed various derivatives of adenosine and theophylline for use as receptor antagonists. The article discloses that hydrophobic substituents are able to potentially enhance affinity. However, it is also acknowledged that such substituents may result in a decrease in solubility thus rendering the antagonists less soluble in vivo. In confronting these problems, Jacobson et al. indicates that a dipropyl substitution at the 1 and 3 positions of theophylline allows desirable affinity at $A_1$ receptors. It is also stated that substitutions at the 7-position are typically not favorable.

It is an object of the present invention to therefore provide compounds useful as $A_1$ adenosine receptor antagonists which display high potency and affinity levels, along with water solubility.

SUMMARY OF THE INVENTION

In one aspect, the present invention provides a compound of the general formula:

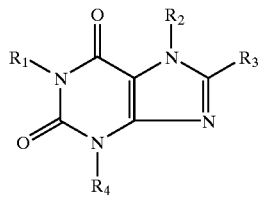

wherein
$R_1$ is selected from the group consisting of $C_1$–$C_8$ alkyl;
$R_2$ is of the formula:

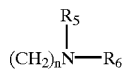

wherein n is an integer ranging from 1 to 8; $R_5$ is H or $CH_3(CH_2)_p$, wherein p is an integer ranging from 1 to 7; and $R_6$ is H, $(CH_2)_mH$, or $(CH_2)_mOH$, wherein m is an integer ranging from 1 to 8;
$R_3$ is selected from the group consisting of:

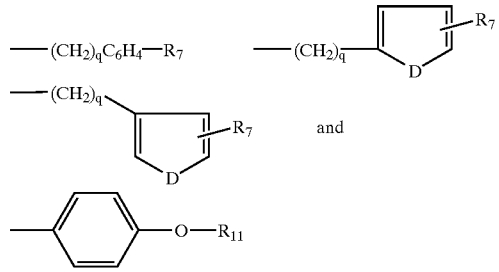

wherein q is an integer ranging from 1 to 8; D is selected from the group consisting of S, NH, and O and wherein $R_7$ is selected from the group consisting of H, OH, $NH_2$, $R_9COOH$, wherein $R_9$ is an alkylene or alkenylene group having 1 to 8 carbon atoms, and $(CH_2)_tOH$, wherein t is an integer ranging from 1 to 8; wherein $R_{11}$ is selected from the group consisting of $-CH_2COOH$ and $-CH_2-CONH(CH_2)_wNHZ$, wherein w is an integer ranging from 1 to 2 and Z is selected from the group consisting of hydrogen and acetate; and
$R_4$ is of the formula:

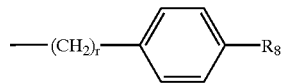

wherein $R_8$ is selected from the group consisting of H; OH; $(CH_2)_fNH_2$ wherein f is selected from the group consisting of 0 and an integer ranging from 1 to 8; $(CH_2)_sOH$, wherein s is an integer ranging from 1 to 8; and $R_{10}COOH$, wherein $R_{10}$ is an alkylene or alkenylene group having 1 to 8 carbon atoms; and r is an integer ranging from 1 to 8.

In a second aspect, the invention provides for assay-type probes of the above compound, wherein the probes are marked or conjugated with radioactive or non-radioactive material.

In a third aspect, the invention provides a pharmaceutically acceptable salt of the above compound.

In a fourth aspect, the invention provides a pharmaceutical composition which comprises the above compound and a pharmaceutically acceptable carrier.

DETAILED DESCRIPTION OF THE INVENTION

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The present invention is directed to a compound of the formula (I):

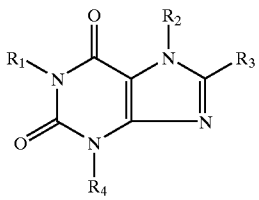

$R_1$ is selected from the group consisting of $C_1$–$C_8$ alkyl, preferably $C_1$ to $C_4$ alkyl. For the purposes of the invention, $R_1$ is more preferably $C_1$ or $C_3$ alkyl, and is most preferably $C_3$ alkyl.

$R_2$ is of the formula:

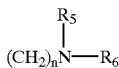

wherein n is an integer ranging from 1 to 8, more preferably 1 to 4; $R_5$ is H or $CH_3(CH_2)_p$, wherein p is an integer ranging from 1 to 7, more preferably 1 to 4; and $R_6$ is H, $(CH_2)_mH$, or $(CH_2)_mOH$, wherein m is an integer ranging from 1 to 8, more preferably 1 to 4.

$R_3$ is selected from the group consisting of:

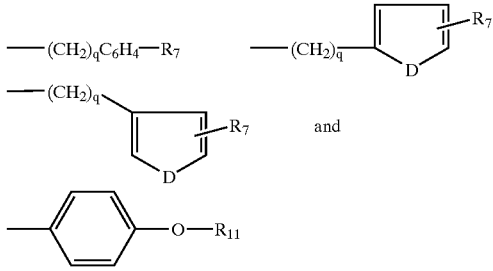

wherein q is an integer ranging from 1 to 8; D is selected from the group consisting of S, O, and NH; and wherein $R_7$ is selected from the group consisting of H, OH, $NH_2$, $R_9COOH$, wherein $R_9$ is an alkylene or alkenylene group having 1 to 8 carbon atoms, and $(CH_2)_tOH$, wherein t is an integer ranging from 1 to 8. The alkylene or alkenylene groups may be substituted or unsubstituted. $R_9$ is preferably CH=CH. $R_{11}$ is selected from the group consisting of —$CH_2COOH$ and —$CH_2$—$CONH(CH_2)_wNHZ$, wherein w is an integer ranging from 1 to 2 and Z is selected from the group consisting of hydrogen and acetate.

$R_4$ is of the formula:

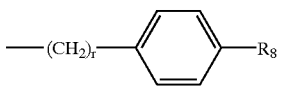

wherein $R_8$ is selected from the group consisting of H; OH; $(CH_2)_fNH_2$, wherein f is selected from the group consisting of 0 and an integer ranging from 1 to 8; $(CH_2)_sOH$, wherein s is an integer ranging from 1 to 8, more preferably 1 to 4; and $R_{10}COOH$, wherein $R_{10}$ is an alkylene or alkenylene group having 1 to 8 carbon atoms; and r is an integer ranging from 1 to 8, more preferably 1 to 4. In the above, $R_9$ and $R_{10}$ are preferably CH=CH.

The invention may be illustrated below with respect to preferred embodiments. In these embodiments, $R_3$ is of the formula:

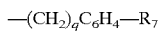

In one preferred embodiment, $R_1$ is $C_3$ alkyl; $R_5$ is $CH_3(CH_2)_p$ wherein p is 1; $R_6$ is $(CH_2)_mOH$ wherein m is 2; $R_7$ is H; $R_8$ is $NH_2$; f is 0; n is 2; m is 2; q is 1; and r is 2.

In another preferred embodiment, $R_1$ is $C_3$ alkyl; $R_5$ is $CH_3(CH_2)_p$ wherein p is 1; $R_6$ is H; $R_7$ is $NH_2$; $R_8$ is $NH_2$; f is 0; n is 2; q is 1; and r is 2.

In another preferred embodiment, $R_1$ is $C_3$ alkyl; $R_5$ is $CH_3(CH_2)_p$ wherein p is 1; $R_6$ is H; $R_7$ is H; $R_8$ is $NH_2$; f is 0; n is 2; q is 1; and r is 2.

In another preferred embodiment, $R_1$ is $C_3$ alkyl; $R_5$ is $CH_3(CH_2)_p$ wherein p is 1; $R_6$ is H; $R_7$ is H; $R_8$ is selected from the group consisting of $(CH_2)_sOH$, wherein s is 2 and $R_{10}COOH$, wherein $R_{10}$ is CH=CH; n is 2; q is 1; and r is 2.

In another preferred embodiment, $R_1$ is $C_3$ alkyl; $R_5$ is $CH_3(CH_2)_p$ wherein p is 1; $R_6$ is H; $R_7$ is selected from the group consisting of $R_9COOH$, wherein $R_9$ is CH=CH and $(CH_2)_tOH$, wherein t is 2; $R_8$ is $NH_2$; f is 0; n is 2; q is 1; and r is 2.

The compound of the present invention may form pharmaceutically acceptable salts with both organic and inorganic acid and bases. Examples of suitable acids for salt formation are hydrochloric, sulfuric, phosphoric, acetic, citric, oxalic, malonic, salicylic, ascorbic, maleic, methanesulfonic, and the like. Any of the amine acid addition salts may also be used. The salts are prepared by contacting the free base form of the compound with an appropriate amount of the desired acid in a manner known to one skilled in the art. Examples of suitable bases for salt formation are sodium hydroxide, sodium carbonate, sodium bicarbonate, potassium hydroxide, calcium hydroxide, ammonia, organic amines, and the like. The salts may be prepared by contacting the free acid form of the compound with an appropriate amount of the desired base in a manner known to one skilled in the art.

The invention also provides $A_1$ adenosine receptor antagonist compounds with radioactive or non-radioactive labels. Such labelled compounds are useful as assay-type probes or conjugates, and may be used to obtain quantitative binding measurements of the $A_1$ adenosine receptor antagonist compounds. For the purposes of the invention, "assay-type probes" refers to those materials which are useful for enhancing the selectivity of the quantitative analysis of the $A_1$ adenosine receptor compounds of the invention. Examples of such assay-type probes are described in U.S. Pat. No. 5,248,770 to Jacobson et al., the disclosure of which is incorporated herein by reference in its entirety. The probes are highly useful in that they have little adverse effect on the affinity of the compounds of the present invention. Radioactive markers include, but are not limited to, an electric spin marker, a $^{19}F$ NMR probe, a radioactive $^{18}F$ isotope marker, a radioactive iodine marker (e.g., $^{125}I$), a radioactive $^3H$ marker, tritium, and a complex of a metal atom or a metal ion and a chelating agent. An exemplary metal ion is a radioactive isotope of technetium or indium. An exemplary chelating agent is diethylene pentacetic anhydride.

Various non-radioactive materials may be used in labelling the present $A_1$ adenosine receptor compounds. Numerous examples are presented in U.S. Pat. No. 5,248,770 to Jacobson et al. Biotin is used as a common non-radioactive label for such probes, as described in R. W. Old et al. *Principals of Gene Manipulation*, 4th ed: 328–331 (1989). To facilitate labelling the compounds with biotin or any other appropriate material, a spacer component may be added to the compound according to an accepted method. Such a method is described in the Jacobson et al. '770 patent. Exemplary spacer components include, but are not limited to, an oligopeptide, triglycidyl, and N-hydroxysuccinimide ester.

Biotin may be bonded to any suitable linkage provided by substituents on the compound structure in accordance with any accepted and suitable technique. For example, referring to compound (I) as defined herein, biotin may be bonded to the hydroxy group on $R_6$ when the compound contains $(CH_2)_mOH$ at $R_6$ with m defined herein; to the amino group present on either of $R_7$ or $R_8$ when $(CH_2)_fNH_2$ is contained at the $R_8$ position, wherein f is defined herein; to the hydroxyl group present as $R_7$ or $R_8$; or to the carboxyl group present when $R_7$ and $R_8$ are $R_9COOH$ or $R_{10}COOH$ respectively, with $R_9$ and $R_{10}$ defined herein. Additionally, the biotin may be bonded to a hydroxyl group present on $R_8$, when $R_8$ is $(CH_2)_sOH$ with s being defined herein. Biotin may also be bonded to $R_7$, when $R_7$ is $(CH_2)_tOH$ with t being defined herein. The biotin-labeled probes may be detected through appropriate and known analytical techniques.

Fluorescent dyes may also be employed as a non-radioactive labels and are applied to appropriate locations on the compounds of the invention. Such dyes include, but are not limited to, tetramethylrhodamine, fluorescein isothiocyanate, and mixtures thereof. Other non-radioactive materials include for example, nitrobenzoxadiazole; 2,2,6,6-tetramethyl-piperindinyloxy-4-isothiocyanate; and mixtures thereof.

The invention is also directed to a pharmaceutical composition which includes the compound of the present invention and a pharmaceutically acceptable carrier. The pharmaceutical composition is particularly useful in applications relating to organ preservation in vivo or in situ, perfusion of an isolated organ either removed or contained within the body (e.g., when an organ is transported for transplantation), cardiopulmonary bypass, perfusion of an extremity or limb, and the like. The compounds may be used in intra-articular, intra-thecal, gastrointestinal, and genital urinary applications, as well as in any cavity or lumen such as, for example, the thoracic cavity or ear canal.

The pharmaceutical composition may be employed, as an example, in oral dosage form as a liquid composition. Such liquid compositions can include suspension compositions or syrup compositions and can be prepared with such carriers as water; a saccharide such as sucrose, sorbitol, fructose, and the like; a glycol such as polyethyleneglycol, polypropyleneglycol, and the like; an oil such as sesame oil, olive oil, soybean oil, and the like; an antiseptic such as p-hydroxy- benzoic acid esters and the like; and a flavor component such as a fruit flavor or a mint flavor. The pharmaceutical composition may also be in the form of powder, pills, capsules, and tablets and can be prepared with various carriers. Suitable carriers include, but are not limited to, lactose, glucose, sucrose, mannitol, and the like; disintegrators such as starch, sodium alginate, and the like; binders such as polyvinyl alcohol, hydroxypropyl cellulose, gelatin, and the like; surfactants such as, for example, fatty acid esters; and plasticizers such as, for example, glycerins. The composition of the present invention is especially useful when applied sublingually. It should be noted that in the preparation of the tablets and capsules, a solid pharmaceutical carrier is used. Advantageously, the pharmaceutical composition may be used in the form of, for example, eye drops or an aerosol.

Other types of pharmaceutical compositions may be employed in the form of a suppository, a nasel spray, and an injectable solution. These compositions are prepared using appropriate aqueous solutions which may include, but are not limited to, distilled water, and saline and buffer additives. Other components may be employed such as organic materials including neutral fatty bases. Additionally, the pharmaceutical composition may be utilized in a transdermal application.

Biopolymers may be used as carriers in the above pharmaceutical compositions. Exemplary biopolymers may include, for example, proteins, sugars, or lipids.

The $A_1$ receptor antagonists of the present invention are particularly useful as, for example, anti-allergenics, CNS stimulants, diuretics, anti-asthmatics, and cardiotonics.

Selective analogues of adenosine receptor antagonists have been developed through the "functionalized congener" approach. See e.g., U.S. Pat. No. 4,968,672 to Jacobson et al.; and Jacobson et al., *Mol. Pharmacol.* 29: 126–133 (1985). In terms of pharmacology, the compounds advantageously display increased affinity at $A_1$ receptor sites relative to former $A_1$ receptor antagonists while simultaneously exhibiting good water solubility.

The foregoing example is illustrative of the present invention, and is not to be construed as limiting thereof.

EXAMPLE

Synthesis of $A_1$ Adenosine Receptor Antagonists $A_1$ adenosine receptor antagonists of the present invention may be synthesized according to the process illustrated below:

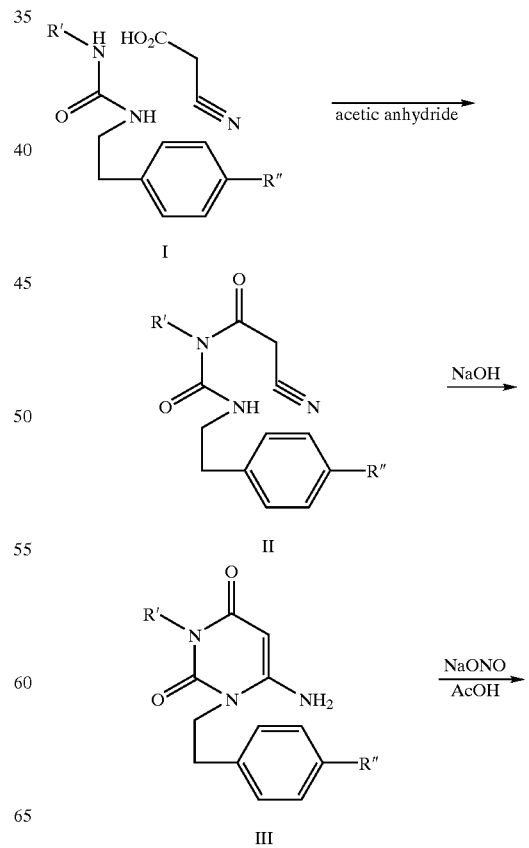

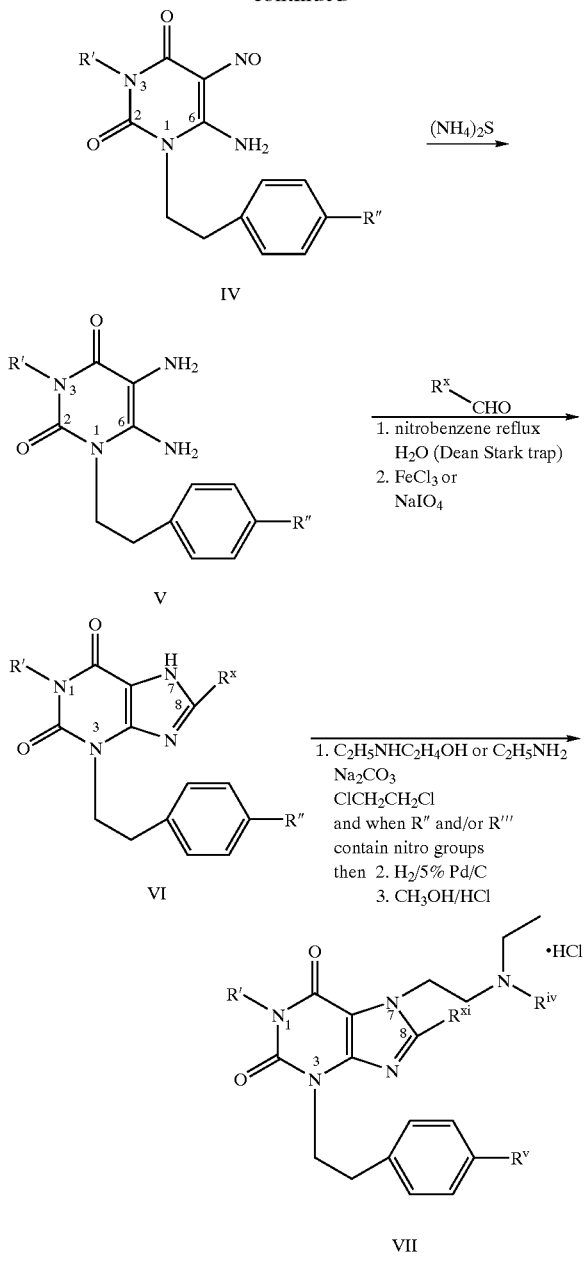

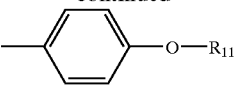

wherein R''' may be selected from the group consisting of H, OH, NO$_2$, R$_9$COOH, wherein R$_9$ is an alkylene or alkenylene group having 1 to 8 carbon atoms, and (CH$_2$)$_t$OH, wherein t is an integer ranging from 1 to 8; D may be selected from the group consisting of O, S, and NH; q is an integer ranging from 1 to 8; R$_{11}$ is selected from the group consisting of —CH$_2$COOH and —CH$_2$—CONH(CH$_2$)$_w$NHZ, wherein w is an integer ranging from 1 to 2 and Z is selected from the group consisting of hydrogen and acetate; and R$^{iv}$ may be selected from the group consisting of H, (CH$_2$)$_m$H, and (CH$_2$)$_m$OH, wherein m is an integer ranging from 1 to 8. As identified in formula (VII), R$^v$ may be selected from the group consisting of H; OH; (CH$_2$)$_f$NH$_2$ wherein f is selected from the group consisting of 0 and an integer ranging from 1 to 8; (CH$_2$)$_s$OH, wherein s is an integer ranging from 1 to 8; and R$_{10}$COOH, wherein R$_{10}$ is an alkylene or alkenylene group having 1 to 8 carbon atoms. R$_{xi}$ may be selected from the group consisting of:

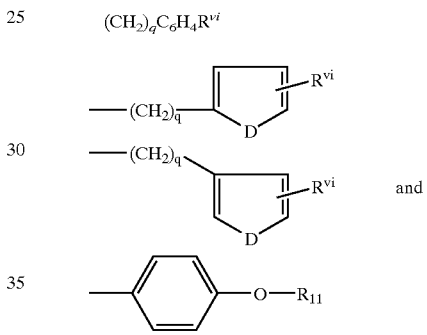

wherein D may be selected from the group consisting of O, S, and NH; q is an integer ranging from 1 to 8; R$^{vi}$ may be selected from the group consisting of H, OH, NH$_2$, R$_9$COOH, wherein R$_9$ is an alkylene or alkenylene group having 1 to 8 carbon atoms, and (CH$_2$)$_t$OH, wherein t is an integer ranging from 1 to 8. R$_{11}$ is selected from the group consisting of —CH$_2$COOH and —CH$_2$—CONH(CH$_2$)$_w$NHZ, wherein w is an integer ranging from 1 to 2 and Z is selected from the group consisting of hydrogen and acetate. In general, the above synthesis steps may be carried out at standard temperature and pressure conditions, optionally under reflux. An exception to this pertains to the reaction involving intermediates (VI) and (VII) which is preferably performed at a temperature ranging from about 25° C. to about 50° C. and at atmospheric pressure. In the reaction step involving intermediate (V) becoming intermediate (VI), it is desired to employ an oxidation step with FeCl$_3$ or NaIO$_4$ subsequent to the nitrobenzene reflux. Moreover, it should be noted that when R'' and/or R''' contain nitro groups, a reaction step which involves applying H$_2$ over a Pd/C catalyst is employed prior to the reaction with CH$_3$OH/HCl. The resulting product (VII) may be further processed and purified according to accepted procedures.

In the above reaction pathway, R' may be C$_1$–C$_8$ alkyl; R'' may be selected from the group consisting of H, OH, (CH$_3$)$_e$NO$_2$ wherein e is selected from the group consisting of 0 and an integer ranging from 1 to 8; (CH$_2$)$_s$OH, wherein s is an integer ranging from 1 to 8; and R$_{10}$COOH, wherein R$_{10}$ is an alkylene or alkenylene group having 1 to 8 carbon atom; R$^x$ may be selected from the group consisting of:

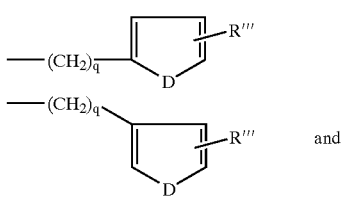

In the specification and example, there have been disclosed typical preferred embodiments of the invention and, although specific terms are employed, they are used in a generic and descriptive sense only and not for purposes of limitation of the scope of the invention being set forth in the following claims.

What is claimed is:
1. A compound of the formula:

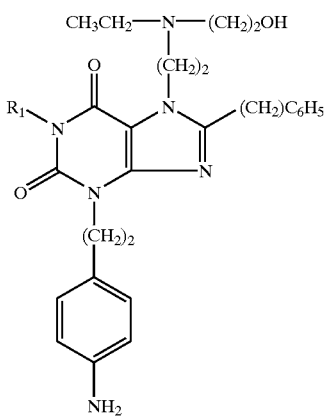

wherein $R_1$ is $C_3$ alkyl.

2. A pharmaceutically acceptable salt of the compound according to claim 1.

3. A pharmaceutical composition comprising a compound according to claim 1 and a pharmaceutically acceptable carrier.

4. A compound of the formula;

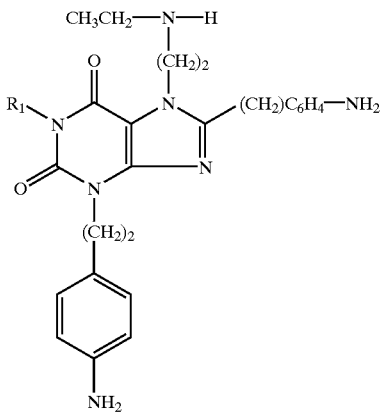

wherein $R_1$ is $C_3$ alkyl.

5. A pharmaceutically acceptable salt of the compound according to claim 4.

6. A pharmaceutical composition comprising a compound according to claim 4 and a pharmaceutically acceptable carrier.

7. A compound of the formula:

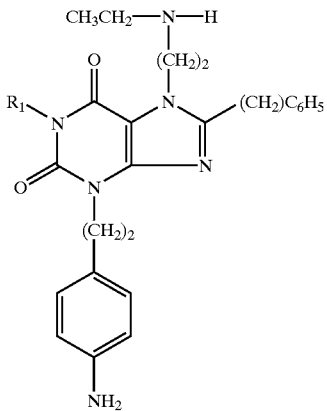

wherein $R_1$ is $C_3$ alkyl.

8. A pharmaceutically acceptable salt of the compound according to claim 7.

9. A pharmaceutical composition comprising a compound according to claim 7 and a pharmaceutically acceptable carrier.

10. A compound of the formula:

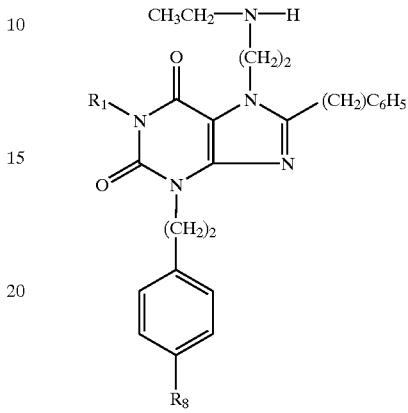

wherein $R_1$ is $C_3$ alkyl; and wherein $R_8$ is selected from the group consisting of $(CH_2)_2OH$ and $CH=CHCOOH$.

11. A pharmaceutically acceptable salt of the compound according to claim 10.

12. A pharmaceutical composition comprising a compound according to claim 10 and a pharmaceutically acceptable carrier.

13. A compound of the formula:

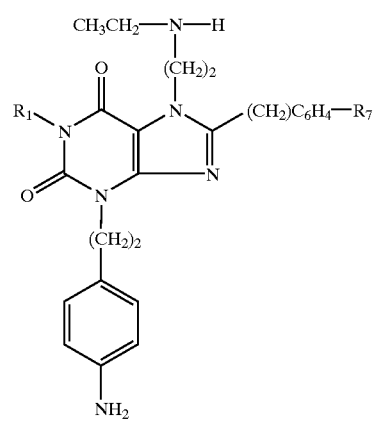

wherein $R_1$ is $C_3$ alkyl; and wherein $R_7$ is selected from the group consisting of $(CH_2)_2OH$ and $CH=CHCOOH$.

14. A pharmaceutically acceptable salt of the compound according to claim 13.

15. A pharmaceutical composition comprising a compound according to claim 13 and a pharmaceutically acceptable carrier.

* * * * *

UNITED STATES PATENT AND TRADEMARK OFFICE
CERTIFICATE OF CORRECTION

PATENT NO. : 6,489,332 B1
DATED : December 3, 2002
INVENTOR(S) : Neely

It is certified that error appears in the above-identified patent and that said Letters Patent is hereby corrected as shown below:

<u>Title page,</u>
Item [57], replace ABSTRACT with the following:

-- A compound useful as an $A_1$ adenosine receptor antagonist has the formula:

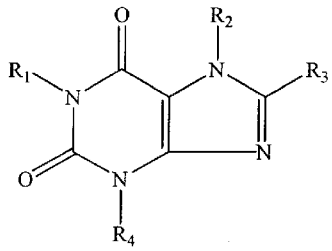

wherein
$R_1$ is selected from the group consisting of $C_1$-$C_8$ alkyl;
$R_2$ is of the formula:

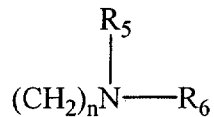

wherein n is an integer ranging from 1 to 8; $R_5$ is H or $(CH_2)_p$, wherein p is an integer ranging from 1 to 8; and $R_6$ is H or $(CH_2)_mOH$, wherein m is an integer ranging from 1 to 8;
$R_3$ is of the formula: —$(CH_2)_qC_6H_4$—$R_7$ wherein q is an integer ranging from 1 to 8; and wherein $R_7$ is selected from the group consisting of H, $NH_2$, $(CH_2)_tOH$, wherein t is an integer ranging from 1 to 8 and $R_9COOH$, wherein $R_9$ is an alkyl or alkylidene group having 1 to 8 carbon atoms; and

UNITED STATES PATENT AND TRADEMARK OFFICE
CERTIFICATE OF CORRECTION

PATENT NO.    : 6,489,332 B1
DATED         : December 3, 2002
INVENTOR(S)   : Neely It is certified that error appears in the above-identified patent and that said Letters Patent is hereby corrected as shown below:

$R_4$ is of the formula:

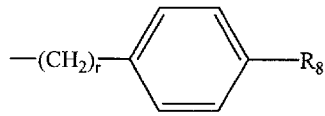

wherein $R_8$ is selected from the group consisting of H; $NH_2$; $(CH_2)_sOH$, wherein s is an integer ranging from 1 to 8; and $R_{10}COOH$, wherein $R_{10}$ is an alkyl or alkylidene group having 1 to 8 carbon atoms; and r is an integer ranging from 1 to 8 --.

Signed and Sealed this

Thirteenth Day of May, 2003

JAMES E. ROGAN
*Director of the United States Patent and Trademark Office*